US012590049B2

(12) United States Patent
McGrath et al.

(10) Patent No.: US 12,590,049 B2
(45) Date of Patent: Mar. 31, 2026

(54) METAL-FREE OXIDATION OF PYRENES

(71) Applicant: Arizona Board of Regents on Behalf of the University of Arizona, Tucson, AZ (US)

(72) Inventors: Dominic V. McGrath, Tucson, AZ (US); Tarek H. El Assaad, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 516 days.

(21) Appl. No.: 18/009,656

(22) PCT Filed: Jun. 11, 2021

(86) PCT No.: PCT/US2021/037131

§ 371 (c)(1),
(2) Date: Dec. 9, 2022

(87) PCT Pub. No.: WO2021/252984

PCT Pub. Date: Dec. 16, 2021

(65) Prior Publication Data

US 2023/0212102 A1 Jul. 6, 2023

Related U.S. Application Data

(60) Provisional application No. 63/038,579, filed on Jun. 12, 2020.

(51) Int. Cl.
*C07C 45/28* (2006.01)

(52) U.S. Cl.
CPC .......... *C07C 45/28* (2013.01); *C07C 2603/50* (2017.05)

(58) Field of Classification Search
CPC ............................ C07C 45/28; C07C 2603/50
See application file for complete search history.

(56) References Cited

U.S. PATENT DOCUMENTS 3,873,580 A * 3/1975 Rennie .................. C07C 205/46
568/309

OTHER PUBLICATIONS

Giri et al. Oxidation of polycyclic aromatic hydrocarbons with hydrogen peroxide catalyzed by iron (III) porphyrins. Catalysis Communications, vol. 10, 383-387. (Year: 2009).*

PCT/US21/37131—PCT International Search Report and Written Opinion, Sep. 30, 2021.

Hu et al., "Ruthenium(III) Chloride Catalyzed Oxidation of Pyrene and 2,7-Disubstitued Pyrenes: An Efficient, One-Step Synthesis of Pyrene-4,5-diones and Pyrene-4,5,9, 10-tetraones," *J. Org. Chem.* 2005, 70, pp. 707-708.

Abdel-Razik et al., "Dielectric Properties of New Fully Conjugated 2H- and Metal-Pyrazino-porphyrazine Network Polymers " *Journal of Applied Polymer Science*, 2011. vol. 121, pp. 3579-3589.

Barathi et al., "Electrochemical Conversion of Unreactive Pyrene to Highly Redox-Active 1,2-Quinone Derivatives on a Carbon Nanotube-Modified Gold Electrode Surface and Its Selective Hydrogen Peroxide Sensing," *Langmuir* 2013. 29, pp. 10617-10623.

Tarek El-Assaad, "Sterically Driven Metal-Free Oxidation of 2,7-di-tert-butylpyrene," *Green Chem.*, Jul. 22, 2020, 22, pp. 5966-5971.

* cited by examiner

*Primary Examiner* — Sikarl A Witherspoon
(74) *Attorney, Agent, or Firm* — BLANK ROME LLP

(57) ABSTRACT

The present invention provides a method for oxidizing pyrenes without any metal-mediated catalyst or reagent. In particular, the present invention provides a method for selectively oxidizing the K-region of pyrenes using a meta-free oxidizing agent to produce a pyrene 4,5-dione and/or a pyrene 4,5,9,10-tetraone compounds.

24 Claims, No Drawings

METAL-FREE OXIDATION OF PYRENES

CROSS-REFERENCE TO RELATED APPLICATIONS

This application is a 371 national stage application of PCT/US21/037131, filed on Jun. 11, 2021, which claims priority to U.S. provisional patent application Ser. No. 63/038,579, filed on Jun. 12, 2020, each of which are hereby incorporated herein by reference in their entireties.

STATEMENT REGARDING FEDERALLY FUNDED RESEARCH

This invention was made with government support under Grant Nos. 1464530 and 1708443 awarded by NSF. The government has certain rights in the invention

FIELD OF THE INVENTION

The present invention relates to a method for oxidizing pyrenes without any metal-mediated catalyst or reagent. In particular, the present invention provides a method for selectively oxidizing the K-region of pyrenes using a metal-free oxidizing agent to produce a pyrene 4,5-dione and/or a pyrene 4,5,9,10-tetraone compounds.

BACKGROUND OF THE INVENTION

Pyrene compounds are polycyclic aromatic hydrocarbon (PAH) molecules that are used widely in various applications including, but not limited to, as fluorescent probes and starting materials for producing various organic electronic components such as organic light emitting diodes (OLEDs), organic field effect transistors (OFETs), and organic photovoltaics (OPVs). Chemical modifications of pyrenes through a variety of methods enable their incorporation into more complex chemical systems. For example, ortho-quinones of pyrene such as pyrene-4,5-dione and pyrene-4,5,9,10-tetraone, and 2,7-disubstituted derivatives, are useful starting materials for larger organic semiconductors as they enable the extension of the π-conjugated system via simple condensation reactions with ortho-diamines. This strategy enables the synthesis of imine rich N-heteroacene chains known as pyrene-fused pyrazaacenes (PPAs) that exhibit a wide range tunable semiconducting properties (p-type to n-type) unlike their nitrogen-free acene counterparts. Owing to the two Clar sextets provided per pyrene subunit, PPAs are air-stable even above 500° C.

Even though ortho-quinones of pyrenes are useful starting materials for the synthesis of PPAs and other organic semiconductors, their synthesis via direct oxidation of pyrene derivatives have been difficult due to the poorer nucleophilicity of the 4,5,9,10-positions in pyrene (known as the K-region) in comparison to the more electron-rich 1,3,6,8-positions. Osmium and ruthenium tetroxides have been among the few oxidants that do oxidize pyrene at the K-region resulting in the 4,5-dione. Unfortunately, use of these transition metal-mediated oxidation results in a relatively poor yield (ca. <22%) of the desired product. Furthermore, these transition metal-mediated oxidation of pyrenes are expensive and results in several undesired byproducts as well as loss of product during isolation due to formation of tarry residue. Moreover, use of these transition metals results in wastes that are environmentally toxic and requires additional cost and time for disposal.

Therefore, there is a need for a method for selectively oxidizing pyrene compounds in the K-region that does not require use of a toxic metal reagent. In addition, there is a need for a method for selectively oxidizing pyrene compounds in the K-region that does not result in a significant formation of undesired byproducts, tarry residues, and/or waste that is detrimental to environment.

SUMMARY OF THE INVENTION

Some aspects of the invention provide a method for oxidizing a pyrene compound of the formula:

I

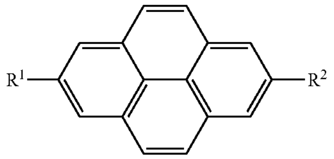

to produce a pyrene 4,5-dione or a pyrene 4,5,9,10-tetraone compound of the formula:

II

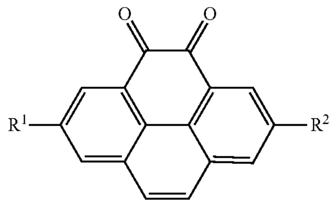

or

III

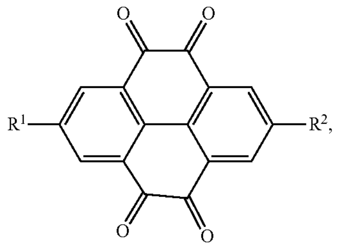

respectively where each of $R^1$ and $R^2$ is independently alkyl, aryl, or heteroaryl. In some embodiments, each of $R^1$ and $R^2$ is independently $C_2$-$C_{20}$ alkyl, often $C_3$-$C_{20}$ alkyl, and most often $C_3$-$C_5$ alkyl. In one particular embodiment, each of $R^1$ and $R^2$ is independently selected from the group consisting of isopropyl, tert-butyl, sec-butyl, isobutyl, tert-pentyl, neopentyl, isopentyl, and sec-pentyl. Still in other embodiments, each of $R^1$ and $R^2$ is independently aryl or heteroaryl.

The method includes contacting pyrene compound of Formula I with a metal-free oxidizing agent under conditions sufficient to produce the desired pyrene 4,5-dione of Formula II and/or pyrene 4,5,9,10-tetraone of Formula III Another aspect of the invention provides a method for producing pyrene 4,5-dione compound of Formula II from a pyrene compound of Formula I. The method includes contacting said pyrene compound of Formula I

I

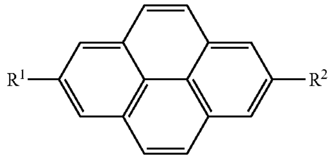

with a less than 6 molar equiv. of a metal-free oxidizing agent under conditions sufficient to produce said pyrene 4,5-dione compound of Formula II:

II

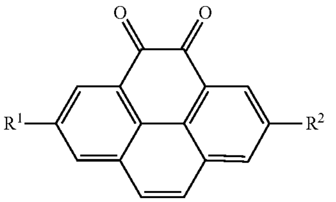

where $R^1$ and $R^2$ are those defined herein. As used herein, the terms "those defined above" and "those defined herein" when referring to a variable incorporates by reference the broad definition of the variable as well as narrower definitions, if any.

Still another aspect of the invention provides a method for producing pyrene 4,5,9,10-tetraone compound of Formula III from a pyrene compound of Formula I, said method comprising contacting said pyrene compound of Formula I

I

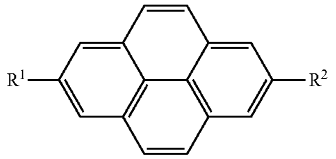

with greater than 6 molar equiv. of a metal-free oxidizing agent under conditions sufficient to produce said pyrene 4,5,9,10-tetraone compound of Formula III:

III

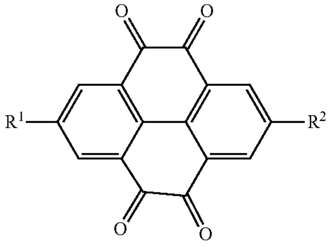

where $R^1$ and $R^2$ are those defined herein.

DETAILED DESCRIPTION OF THE INVENTION

Prior to 2005, indirect multistep synthesis was utilized to produce pyrene 4,5-dione compounds and pyrene 4,5,9,10-tetraone compounds. Such a circuitous route of synthesis resulted in a relatively high cost and an extensive production time, significantly discouraging development and wide use of pyrene compounds in organic semiconductor application. However, with the development of a ruthenium-ion-catalyzed oxidation (RICO) method for a one-pot oxidation of the K-region of pyrene compounds, there was a resurgence of interest in PPAs as organic semiconductors. Unfortunately, however, this method suffered from relatively poor yield (<50%) and difficult workup process exacerbated by the formation of large amounts of dark green and black intractable material, the removal of which contributes to a substantial loss of the desired product and an increase in the amount of solvent used in the process. While some improvements to this RICO method has been developed, e.g., using tetrahydrofuran (THF) as co-solvent instead of acetonitrile (MeCN), that resulted in shorter reaction times and using the additive N-methylimidazole (NMI) which helps clean up the workup by minimizing the formation of the troublesome intractable material, none of the conventional methods significantly changed the isolated yield of the desired product. More significantly, while these improvements addressed the synthesis of diones 2a and 2b, none of these improvements led to a significant yield of the tetraones 3a and 3b. See, FIG. 1.

FIG. 1

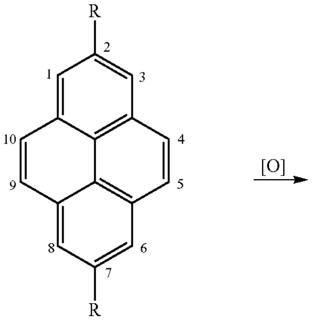

1a (R = H)
1b (R = t-Bu)

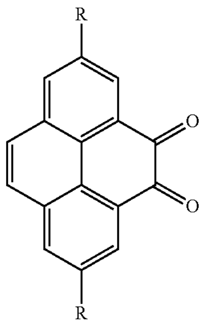

and/or 2a (R = H)
2b (R = t-Bu)

-continued

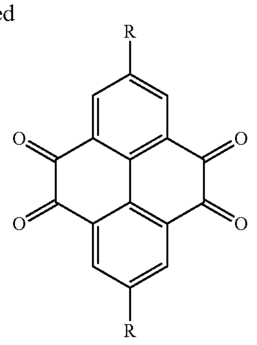

3a (R = H)
3b (R = t-Bu)

Despite the relative success of conventional methods as the only one-pot K-region oxidation of pyrene, these procedures all require ruthenium, chlorinated solvents, and suffer from low yields and are sensitive to reaction time temperature. Moreover, conventional methods frequently result in an unavoidable mixture of 4,5-dione and 4,5,9,10-tetraone and several by-products such as biphenyl and phenanthrene aldehydes. In short, they are resource inefficient from the standpoints of yield, hazardous solvents, requires expensive and toxic transition metal reagent, and the extensive purification procedure.

Methods of the present invention avoids or reduces some, if not all, of these limitations of transition metal-based oxidation of pyrene compounds. In particular, some of the advantages of methods of the invention include, but are not limited to, (i) the use of less expensive oxidizing agents, relative to transition metal reagents such as ruthenium chloride (to generate ruthenium tetroxide); (ii) a metal-free oxidation; (iii) a simple workup and recovery of the desired product; and (iv) a significantly higher yield of the desired products. As such, in some embodiments, the product contains no trace of metal. As used herein, the term “no trace of metal” refers to no detectable amount of metal or alternatively, having less than 5 ppm, typically less than 3 ppm, and often less than 1 ppm of transition metal or heavy metal.

One particular aspect of the invention provides a method for oxidizing a pyrene compound of the formula:

I

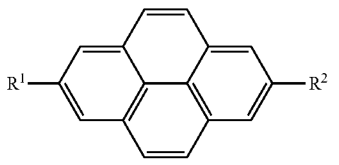

said method comprising contacting said pyrene compound of Formula I with a metal-free oxidizing agent under conditions sufficient to produce a pyrene-4,5-dione or a pyrene-4,5,9,10-tetraone compound of the formula:

II

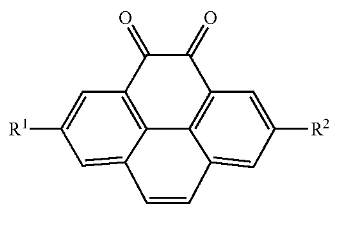

or

-continued

III

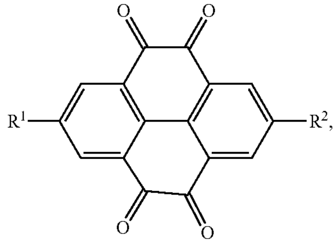

respectively, where each of $R^1$ and $R^2$ is independently alkyl, aryl, or heteroaryl. As used herein, the term “alkyl” refers to a saturated linear monovalent hydrocarbon moiety. Unless the number of carbon atoms is specified, the term “alkyl” typically refers to hydrocarbon moiety having one to twenty, typically one to twelve, often one to eight, and more often one to six carbon atoms or a saturated branched monovalent hydrocarbon moiety of three to twenty, typically three to twelve, often three to eight, and more often three to six carbon atoms. Exemplary alkyl group include, but are not limited to, methyl, ethyl, n-propyl, 2-propyl, tert-butyl, n-pentyl, neopentyl, and the like. The term “aryl” refers to a monovalent mono-, bi- or tricyclic aromatic hydrocarbon moiety of 6 to 15 ring atoms which is optionally substituted with one or more substituents within the ring structure. When two or more substituents are present in an aryl group, each substituent is independently selected. Exemplary substituents for the aryl group include, but are not limited to, alkyl, haloalkyl (i.e., alkyl group where one or more hydrogen is replaced with a halide, including perhaloalkyls such as trifluoromethyl, pentafluoroethyl, etc.), heteroalkyl (e.g., —$XR^a$, where X is O, S, $NR^b$—, $R^a$ is H or alkyl, and $R^b$ is H, alkyl, or a nitrogen protecting group, see, for example, P. G. M. Wuts, *Green's Protective Groups in Organic Synthesis,* $5^{th}$ edition, John Wiley & Sons, New York, 2014, and *Compendium of Synthetic Organic Methods*, Vols. 1-13 (John Wiley and Sons, 1971-2014), which are incorporated herein by reference in their entirety), halide (e.g., F, Cl, Br, or I), nitro, cyano, or optionally substituted phenyl. Exemplary aryls of the invention include, but are not limited to, phenyl, naphthyl, anthracyl, each of which is optionally substituted. In some embodiments, the aryl group is unsubstituted aryl. The term “heteroaryl” means a monovalent monocyclic or bicyclic aromatic moiety of 5 to 20 ring atoms containing one, two, or three ring heteroatoms selected from N, O, or S, the remaining ring atoms being C. The heteroaryl ring is optionally substituted independently with one or more substituents. Exemplary substituents of heteroaryl include exemplary substituents for aryl group listed above. More specifically the term heteroaryl includes, but is not limited to, pyridyl furanyl, thiophenyl, thiazolyl, isothiazolyl, triazolyl, carbazolyl, imidazolyl, oxazolyl, isoxazolyl, pyrrolyl, pyrazolyl, pyrazinyl, pyrimidinyl, benzofuranyl, isobenzofuranyl, benzothiazolyl, benzoisothiazolyl, benzotriazolyl, indolyl, isoindolyl, benzoxazolyl, thiazolyl, isothiazolyl, quinolyl, isoquinolyl, benzimidazolyl, benzisoxazolyl, benzothiophenyl, dibenzofuran, and benzodiazepin-2-one-5-yl, and the like, each of which is optionally substituted with 1, 2, 3, or 4 substituents. Typically, when substituted, heteroaryl or aryl is substituted with electron withdrawing substitutent(s).

In some embodiments, $R^1$ and $R^2$ is independently a sterically hindered alkyl, aryl, or heteroaryl group. Exemplary sterically hindered alkyl groups include, but are not limited to, isopropyl, tert-butyl, sec-butyl, isobutyl, tert-pentyl, neopentyl, isopentyl, sec-pentyl, and the like. Typically, a sterically hindered alkyls are those that do not under go $S_N2$ reactions. Still in other embodiments, each of $R^1$ and $R^2$ is independently aryl or heteroaryl.

Yet in other embodiments, the process of the invention produces said pyrene 4,5-dione compound of Formula II in a yield of about 40% or higher, typically about 50% or higher, often about 60% or higher, still more often at least about 75%, and most often greater than 80%. When referring to a numerical value, the terms "about" and "approximately" are used interchangeably herein and refer to being within an acceptable error range for the particular value as determined by one of ordinary skill in the art. Such a value determination will depend at least in part on how the value is measured or determined, e.g., the limitations of the measurement system, i.e., the degree of precision required for a particular purpose. For example, the term "about" can mean within 1 or more than 1 standard deviation, per the practice in the art. Alternatively, the term "about" when referring to a numerical value can mean ±20%, typically ±10%, often ±5% and more often ±1% of the numerical value. In general, however, where particular values are described in the application and claims, unless otherwise stated, the term "about" means within an acceptable error range for the particular value, typically within one standard deviation.

Still in other embodiments, the amount of said metal-free oxidizing agent used ranges more than about 2 molar equiv. to less than about 4 molar equiv. relative to the amount of said pyrene compound of Formula I. In general, formation of pyrene 4,5-dione compound of Formula II is favored when about 6 molar equiv. or less, typically about 5 molar equiv. or less, and often about 4 molar equiv. or less of metal-free oxidizing agent used relative to said pyrene compound of Formula I. Use of less than about 6 molar equiv. of metal-free oxidizing agent generally favors formation of pyrene 4,5-dione compound of Formula II relative to pyrene 4,5,9,10-tetraone compound of Formula II. In some embodiments, when 4 molar equiv. or less, typically 3 molar equiv. or less, of metal-free oxidizing agent is used, the selectivity of the reaction between compound of Formula II and compound of Formula III is greater than about 75%, typically greater than about 80%, often greater than about 85%, still more often greater than about 90%, and most often greater than about 95%, In one particular embodiment, when about 4 molar equiv. or less, typically about 3 molar equiv. or less, of metal-free oxidizing agent is used, the resulting product ratio of compound of Formula II to compound of Formula III is at least about 90:10, typically at least about 95:5, often at least about 98:2, and most often at least 99:1. Still in another particular embodiment, when at least about 6 molar equiv. of metal-free oxidizing agent is used, the resulting product ratio of compound of Formula III to compound of Formula II is at least about 90:10, typically at least about 95:5, often at least about 98:2, and most often at least 99:1. Thus, methods of the invention can be used to produce either compound of Formula II or compound of Formula III almost exclusively. It should be appreciated that one can perform two separate steps to produce compound of Formula III. For example, one can use conditions to produce compound of Formula II almost exclusively, and then subject compound of Formula II to another oxidation process of the invention to produce compound of Formula III In further embodiments, the process is used to produces said pyrene 4,5,9,10-tetraone compound of Formula III in a yield of about 40% or higher, typically about 50% or higher, often about 60% or higher, more often about 75% or higher, still more often about 80% or higher, and most often about 90% or higher. In general, formation of pyrene 4,5,9,10-tetraone compound of Formula III is favored when the amount of said metal-free oxidizing agent used is about 4 molar equiv. or more, typically about 6 molar equiv. or more, and often 8 molar equiv. or more relative to said pyrene compound of Formula I.

As discussed throughout this disclosure, methods of the invention utilize a metal-free oxidizing agent. In one particular embodiment, the metal-free oxidizing agent is a hypervalent iodine oxyacid. Exemplary hypervalent iodine oxyacids that can be used in methods of the invention include, but are not limited to, $H_5IO_6$, $HIO_3$, $HIO_4$, $HIO_2$, HIO, and the like. Other suitable metal-free oxidizing agents include hypervalent iodane compounds, i.e., organoiodine compounds in the +III or +V oxidation states. Exemplary hypervalent iodane compounds that can be used in methods of the invention include, but are not limited to, 2-iodoxybenzoic acid (IBX), Dess-Martin periodinane (DMP), iodosylbenzene and iodosylarene of the formula Ar—I═O (where Ar is aryl such as phenyl, naphthyl, anthracyl, each of which can be optionally substituted with one or more of the following substituents: $C_1$-$C_8$ alkyl, $C_1$-$C_8$ alkoxy (i.e., —OR, where R is $C_1$-$C_8$ alkyl), halide, an electron-withdrawing groups such as —$NO_2$, —CN, or —(C═O)R (where R is $C_1$-$C_8$ alkyl or $C_1$-$C_8$ alkoxy), bis(acetoxy)iodobenzene and other bis(acetoxyoxy)iodoarenes of the formula Ar—$I(OCOCH_3)_2$, where Ar is as defined herein, bis(trifluoroacetoxy)iodobenzene, and other bis(trifluoroacetoxyoxy)iodoarenes of the formula Ar—$I(OCOCF_3)_2$, where Ar is as defined herein. It should be appreciated that a combination of one or more metal-free oxidizing agents can also be used in methods of the invention. Some of the chemical structures of hypervalent iodine oxyacids and hypervalent iodane compounds that can be used in methods of the invention are shown in Tables 1 and 2 below. In addition, some of the representative results of oxidation of pyrene compound 1b with various metal-free oxidizing agents are shown in Table 3 below.

TABLE 1

Representative organic hypervalent iodanes.

| Ox. State | Reagent | Structure |
|---|---|---|
| III | Iodosylarenes<br>Bis(acyloxy)-iodoarenes | Ar—I═O<br>Ar—$I(OCOR)_2$<br>(R = $CH_3$: PIDA)<br>(R = $CF_3$: BTI) |
| | Iodylarenes | 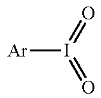 |
| V | Pseudocyclic iodylarenes | 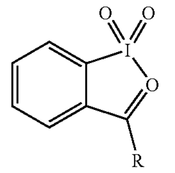 |
| | IBX | 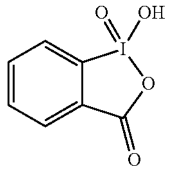 [SMILES: O=C1OI(=O)(O)c2ccccc21] |

TABLE 1-continued

| Representative organic hypervalent iodanes. | | |
|---|---|---|
| Ox. State | Reagent | Structure |
| | DMP | 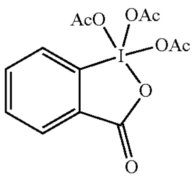 [SMILES: CC(=O)OI1(OC(C)=O)(OC(C)=O)OC(=O)c2ccccc21] |

TABLE 2

| Name | Formula | Structure | Oxid. State | pKa |
|---|---|---|---|---|
| Hypoiodous acid | HIO | 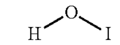 | +I | 11 |
| Iodous acid | $HIO_2$ | 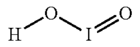 | +III | 4.5 |
| Iodic acid | $HIO_3$ | 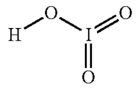 | +V | 0.77 |
| Periodic acid | $HIO_4/H_5IO_6$ | 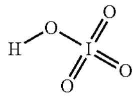 or 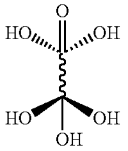 | +VII | 3.29 ($H_3IO_6$) |

Representative Oxyacids of iodine.

TABLE 3

Representative results on pyrene oxidation with some of the hypervalent iodine reagents

| Substrate | Reagent | Solvent(s) | Maj. Product | Yield |
|---|---|---|---|---|
| 1b | $H_5IO_6$ | EtOH | 2b | 75% |
| 1b | $HIO_3$ | iPrOH | 2b | 83% |
| 1b | $I_2/HIO_3$ | EtOH/AcOH | 2b | 60% |
| 1b | $HIO_3$ or $H_5IO_6$ | AcOH (cat. $H_2SO_4$) | 3b | 54% |

Some of the advantages of using a metal-free oxidizing agent instead of using conventional methods that use a metal (in particular transition metal)-mediated oxidation, e.g., RICO, include, but are not limited to, cheaper reagents, greener reaction conditions (i.e., less toxic or hazardous materials), higher yield, and improved chemical selectivity. In fact, the present inventors have found that even after purification, the product(s) obtained using RICO contained a trace amount of ruthenium in the product mixture (data not shown).

The process can include using a solvent. Typical solvents that can be used in methods of the invention include protic solvents, in particular polar protic solvents, such as alcohol, carboxylic acid, water, and a mixture thereof. Exemplary alcohols that can be used as solvents in methods of the invention include, but are not limited to, alcohols with the general formulas $C_nH_{2n+2}O$, $C_nH_{2n}O$, and a mixture thereof. Specific examples of alcohols that can be used as solvents in methods of the invention include, but are not limited to, ethanol, n-propanol, isopropanol, n-butyl alcohol, iso-butyl alcohol, t-butyl alcohol, sec-butyl alcohol, tert-pentyl alcohol, neopentyl alcohol, isopentyl alcohol, sec-pentyl alcohol, cyclopentanol, cyclohexanol, and a mixture thereof. Exemplary carboxylic acids that can be used as solvents in methods of the invention include, but are not limited to, carboxylic acids with the general formulas $C_nH_{2n}O$, $C_nH_{2n-2}O$, and a mixture thereof. Specific examples of carboxylic acids that can be used as solvents in methods of the invention include, but are not limited to, formic acid, acetic acid, propionic acid, butyric acid, pentanoic acid, cyclopentanecarboxylic acid, cyclohexanecarboxylic acid, and a mixture thereof. It should be appreciated that unless explicitly limited, stated, or the context requires otherwise, the term "a mixture thereof" means a mixture of two or more of the listed components. Thus, it can be a mixture of two, three, four or more components.

Other solvents such as water, ethyl acetate (EtOAc), acetone, dimethylsulfoxide ("DMSO"), acetonitrile ("MeCN"), toluene, tetrahydrofuran ("THF"), heptane can also be added as a cosolvent. Some of the other solvents used in methods of the invention are provided in Table 4 below.

TABLE 4

Representative solvents for methods of the invention

| Solvent | Class[a] | bp (° C.) | ε | Solubility[b] | $H_2O$ Soluble[c] |
|---|---|---|---|---|---|
| Water | PP | 100 | 80 | – | — |
| EtOH | PP | 78 | 24 | + | M |
| i-PrOH | PP | 83 | 18 | + | M |
| t-BuOH | PP | 83 | 12 | + | M |
| n-Pentanol | PP | 138 | 14 | + | 2.2 |
| n-Octanol | PP | 195 | 10 | + | 0.1 |
| Ethylene Glycol | PP | 197 | 41 | + | M |
| EtOAc | PA | 77 | 6.0 | + | 8.7 |
| Acetone | PA | 56 | 21 | + | M |
| DMSO | PA | 189 | 47 | + | M |
| MeCN | PA | 82 | 38 | + | M |
| AcOH | PP, Acidic | 118 | 6.2 | + | M |
| $HCO_2H$ | PP, Acidic | 102 | 58 | + | M |
| Toluene | Ar-HC | 111 | 2.4 | ++ | 0.05 |
| Heptane | HC | 98 | 1.9 | + | 0.0003 |
| DCM | Halo-HC | 40 | 9.1 | ++ | 1.3 |

[a]PP (polar protic), PA (polar aprotic), Ar (aromatic), HC (hydrocarbon), Halo (halogenated)

[b]– = insoluble at any temperature, + = fairly soluble at high temperature, ++ = fairly soluble at room temperature;

[c]In grams per 100 mL solvent: M = miscible

The product distribution (e.g., 4,5-dione ("dione") or 4,5,9,10-tetraone ("tetraone")) can be affected by a variety of factors including, but not limited to, solvent acidity, amount of metal-free oxidizing agent used, and the particular metal-free oxidizing agent used. For example, when 3 equiv. of $HIO_3$ in refluxing isopropanol (90 minutes) was used, almost exclusively the product was pyrene 4,5-dione 2b in 83% yield (~1 gram scale, where $R^1$ and $R^2$=t-bu). Similarly, high purity dione 2b was isolated from the reaction of 1b using 2 equiv. $H_5IO_6$ in refluxing ethanol in 75% yield (~1 gram scale). See Scheme 1 below. Increasing $H_5IO_6$ beyond 2 equiv resulted in lower yield of 2b due to formation of tetraone 3b. However, 4 equiv. $H_5IO_6$ (or 6 equiv. of $HIO_3$) in glacial AcOH with catalytic $H_2SO_4$ led to the formation of tetraone 3b in 54% yield (~1 gram scale) in the absence of unreacted starting material 1b or even dione 2b.

SCHEME 1

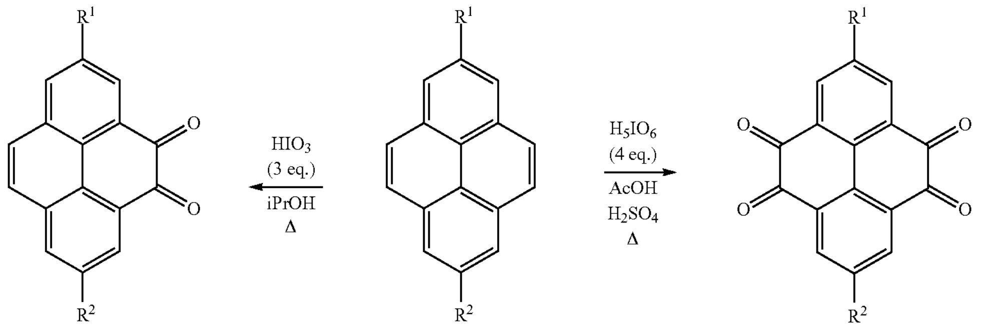

2b 1b 3b where $R^1$ and $R^2$ are those defined herein.

As can be seen acidic solvents appear to favor formation of pyrene 4,5,9,10-tetraone compound of Formula III in favor of pyrene 4,5-dione compound of Formula II. Accordingly, in some embodiments, methods of the invention are conducted in an acidic solvent. Suitable acidic solvent conditions can be produced by using a carboxylic acid, as discussed herein, and can also include adding a non-organic acid such as, but not limited to, sulfuric acid, hydrochloric acid, nitric acid, phosphonic acid, chloric acid, perchloric acid, hydrobromic acid, hydroiodic acid, and a mixture thereof.

Surprisingly and unexpectedly, methods of the invention are exceedingly effective for the oxidation of pyrene compound Formula I into the corresponding pyrene 4,5-dione of Formula II and pyrene 4,5,9,10-tetraone of Formula III. As discussed above, the high selectivity for either pyrene 4,5-dione of Formula II or pyrene 4,5,9,10-tetraone of Formula III can be readily achieved by the amount and the nature of the metal-free oxidizing agent as well as the solvent (e.g., acidity of the solvent) used. Unlike conventional methods that utilize RICO, methods of the invention completely eliminate the formation of dark problematic impurities, significantly improve yield, and lead to a much more resource-efficient workup. In some embodiments, methods of the invention produce the pyrene 4,5-dione of Formula II in at least about 40%, typically at least about 50%, often at least about 55%, and more often about 60% or more. Yet in other embodiments, methods of the invention produce the pyrene 4,5,9,10-tetraone of Formula III in at least about 40%, typically at least about 50%, often at least about 55%, and more often about 60% or more.

Diones (compound of Formula II) and tetraones (compound of Formula III) can be further modified to produce PPAs that can be used in various applications including, but not limited to, as fluorescent probes and starting materials for producing various organic electronic components such as organic light emitting diodes (OLEDs), organic field effect transistors (OFETs), and organic photovoltaics (OPVs). Chemical modifications of pyrenes through a variety of methods for use as more complex chemical systems are well known to one skilled in the art. For example, ortho-quinones of pyrene such as pyrene-4,5-dione and pyrene-4,5,9,10-tetraone, and 2,7-disubstituted derivatives, are useful starting materials for larger organic semiconductors. Furthermore, compounds of the invention can be used to produce imine rich N-heteroacene chains known as pyrene-fused pyrazaacenes (PPAs) that exhibit a wide range tunable semiconducting properties (p-type to n-type). An exemplary method for producing PPAs is illustrated in Scheme II below:

SCHEME II

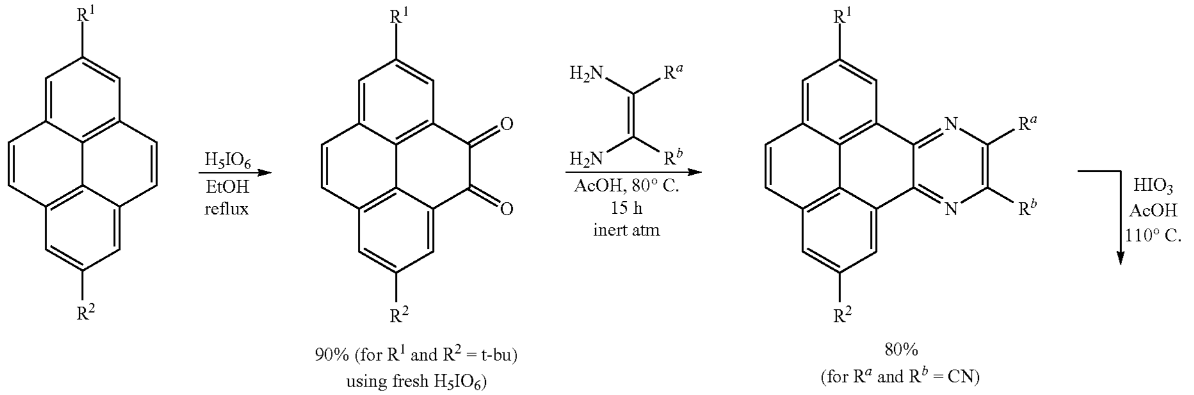

90% (for $R^1$ and $R^2$ = t-bu) using fresh $H_5IO_6$)

80% (for $R^a$ and $R^b$ = CN)

-continued

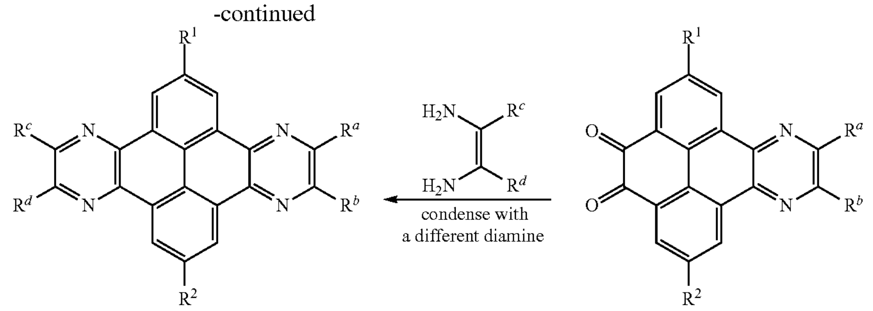

enables easy access to non-symmetrical PPAs with high yields and no purification (single product)

85%
oxidized PPA

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Synthesis of 2,7-Di-tert-butylpyrene-4,5-dione (2b). A mixture of 1b (1.00 g, 3.18 mmol, 1.0 equiv.) and $H_5IO_6$ (1.81 g, 7.95 mmol, 2.5 equiv.) and EtOH (50 mL, 95%) was maintained at reflux for 3 h. The reaction color changed from colorless to yellow to orange to red over that period. After complete conversion was confirmed by TLC, the homogenous dark red reaction mixture was allowed to cool to room temperature ("RT"). Compound 2b slowly crystallized upon cooling. Water (50 mL) was added and the mixture was further cooled in an ice bath for 2 h. The orange precipitate was collected by vacuum filtration and washed with cold water (3×100 mL). The crude solid was purified by filtration through a silica plug (9:1 heptane/EtOAc) to remove inorganic contaminants. Solvent was removed under reduced pressure to provide dione 2b (0.820 g, 2.38 mmol, 75%) as orange solid: mp 240-242° C.; $^1H$ NMR ($CDCl_3$, 400 MHz): δ8.54 (d, J=2.0 Hz, 2H), 8.12 (d, J=2.0 Hz, 2H), 7.79 (s, 2H), 1.49 (s, 18H); 13C NMR ($CDCl_3$, 100 MHz): δ181.0 (Cq), 151.1 (Cq), 131.9 (Cq), 131.8 (CH), 129.7 (Cq), 128.35 (CH), 127.3 (CH), 126.5 (Cq), 35.2 (Cq), 31.2 (CH3); IR (KBr, $\nu_{max}$) 1672 cm-1; UV-Vis (EtOH, $\lambda_{max}$) 440 nm; HRMS (ESI/Orbitrap) m/z: $[M+H]^+$ Calcd. for $C_{24}H_{25}O_2$ 345.1849. Found 345.1835.

Synthesis of 2,7-Di-tert-butylpyrene-4,5,9,10-tetraone (3b). A mixture of 1b (1.00 g, 3.18 mmol, 1.0 equiv.), $HIO_3$ (3.36 g, 19.1 mmol, 6.0 equiv), AcOH (45 mL, 95%), and aqueous $H_2SO_4$ (0.184 M; 5 mL, 0.92 mmol, 0.3 equiv.) was maintained at 50° C. for 16 h. After complete conversion was confirmed by TLC, the dark orange reaction mixture was allowed to cool to RT and poured in water (ca. 100 mL). The mixture was then cooled in an ice bath for 2 h, and the resultant orange precipitate was collected by vacuum filtration and washed with cold water (3×100 mL). The collected precipitate was purified by filtration through a silica plug (4:1 heptane/EtOAc) to remove inorganic contaminants. Solvent was removed under reduced pressure to provide 3b (0.670 g, 1.79 mmol, 56%) as an orange solid: mp>300° C.; $^1H$ NMR ($CDCl_3$, 400 MHz): δ8.48 (s, 4H), 1.43 (s, 18H); $^{13}C$ NMR ($CDCl_3$, 100 MHz): δ178.2 (Cq), 154.8 (Cq), 133.9 (CH), 132.2 (Cq), 130.5 (Cq), 35.4 (Cq), 30.7 ($CH_3$); IR (KBr, $\nu_{max}$) 1676 $cm^{-1}$; UV-Vis (EtOH, $\lambda_{max}$) 421 nm; HRMS (ESI/Orbitrap) m/z: $[M+H]^+$ Calcd. for $C_{24}H_{23}O_4$ 375.1591. Found 375.1580.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A process for oxidizing a pyrene compound according to Formula I:

I

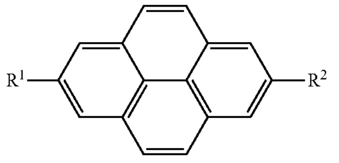

the process comprising contacting the pyrene compound according to Formula I with a metal-free oxidizing agent under conditions sufficient to produce a pyrene 4,5-dione according to Formula II or a pyrene 4,5,9,10-tetraone compound according to Formula III:

II

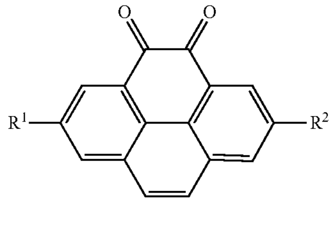

or

-continued

III

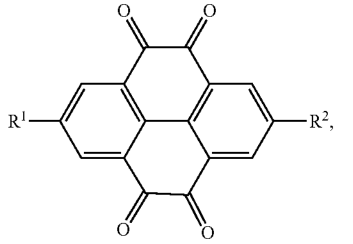

wherein each of $R^1$ and $R^2$ are independently an alkyl, an aryl, or a heteroaryl, and the metal-free oxidizing agent comprises a hypervalent iodine oxyacid, a hypervalent iodine, or any mixture thereof.

2. The process of claim 1, wherein each of $R^1$ and $R^2$ are independently an alkyl selected from the group consisting of isopropyl, tert-butyl, sec-butyl, isobutyl, tert-pentyl, neopentyl, isopentyl, and sec-pentyl.

3. The process of claim 1, wherein each of $R^1$ and $R^2$ are independently an aryl or a heteroaryl.

4. The process of claim 1, wherein the process produces a pyrene 4,5-dione compound according to Formula II in a yield of greater than about 40%.

5. The process of claim 4, wherein the amount of the metal-free oxidizing agent used in the process ranges from more than about 2 molar equivalents to less than about 4 molar equivalents relative to the pyrene compound according to Formula I.

6. The process of claim 1, wherein the process produces a pyrene 4,5,9,10-tetraone compound according to Formula III in a yield of greater than about 40%.

7. The process of claim 6, wherein the amount of the metal-free oxidizing agent used is more than about 4 molar equivalents relative to the pyrene compound according to Formula I.

8. The process of claim 1, wherein said process the conducted using a solvent selected from the group consisting of alcohols, carboxylic acids, water, and any mixture thereof.

9. The process of claim 8, wherein the alcohols comprise ethanol, n-propanol, isopropanol, n-butyl alcohol, iso-butyl alcohol, t-butyl alcohol, sec-butyl alcohol, tert-pentyl alcohol, neopentyl alcohol, isopentyl alcohol, sec-pentyl alcohol, cyclopentanol, cyclohexanol, or any mixture thereof.

10. The process of claim 8, wherein the carboxylic acids comprise formic acid, acetic acid, propionic acid, butyric acid, pentanoic acid, cyclopentanecarboxylic acid, cyclohexanecarboxylic acid, or any mixture thereof.

11. The process of claim 1, wherein the process is conducted using a solvent selected from the group consisting of alcohols, water, and any mixture thereof.

12. The process of claim 1, wherein the hypervalent iodine oxyacid comprises $H_5IO_6$, $HIO_3$, $HIO_4$, $HIO_2$, HIO, or any mixture thereof.

13. The process of claim 1, wherein the hypervalent iodine comprises 2-iodoxybenzoic acid (IBX), Dess-Martin periodinane (DMP), iodosylbenzene, iodosylarene of the formula Ar—I═O, bis(acetoxy)iodobenzene, bis(acetoxyoxy)iodoarenes of the formula Ar—I$(OCOCH_3)_2$, bis(trifluoroacetoxy)iodobenzene, bis(trifluoroacetoxyoxy)iodoarenes of the formula Ar—I$(OCOCF_3)_2$, wherein Ar is an unsubstituted aryl, or Ar is an aryl substituted with one or more of the following substituents: a $C_1$-$C_8$ alkyl, a $C_1$-$C_8$ alkoxy, a halide, and an electron-withdrawing group.

14. A method for producing a pyrene 4,5-dione compound according to Formula II from a pyrene compound according to Formula I, the method comprising:

contacting the pyrene compound according to Formula I;

I

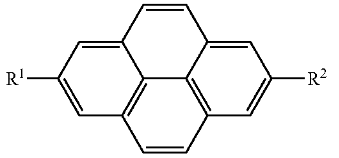

with less than 6 molar equivalents of a metal-free oxidizing agent under conditions sufficient to produce the pyrene 4,5-dione compound according to Formula II:

II

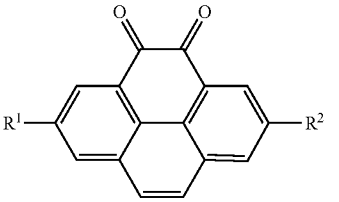

wherein each of $R^1$ and $R^2$ are independently alkyl, aryl, or heteroaryl, wherein the metal-free oxidizing agent comprises a hypervalent iodine oxyacid, a hypervalent iodine, or any mixture thereof.

15. The method of claim 14, wherein the method further comprises using a polar protic solvent.

16. The method of claim 15, wherein the polar protic solvent comprises an alcohol.

17. The method of claim 16, wherein the alcohol is selected from the group consisting of methanol, ethanol, isopropyl alcohol, or a mixture thereof.

18. A method for producing a pyrene 4,5,9,10-tetraone compound according to Formula III from a pyrene compound according to Formula I, the method comprising:

contacting the pyrene compound according to Formula I:

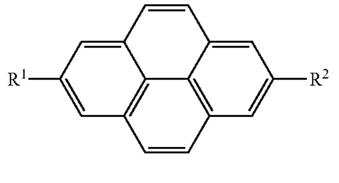

with greater than 6 molar equivalents of a metal-free oxidizing agent under conditions sufficient to produce the pyrene 4,5,9,10-tetraone compound according to Formula III:

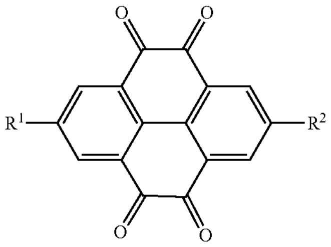

III wherein each of $R^1$ and $R^2$ are independently alkyl, aryl, or heteroaryl, and wherein the metal-free oxidizing agent comprises a hypervalent iodine oxyacid, a hypervalent iodine, or any mixture thereof.

19. The method of claim 18, wherein the method further comprises using an acidic solvent.

20. The method of claim 19, wherein the acidic solvent comprises a carboxylic acid solvent, a sulfonic acid, an organophosphonic acid, or any mixture thereof.

21. The method of claim 20, wherein the carboxylic acid solvent comprises formic acid, acetic acid, propionic acid, butyric acid, pentanoic acid, cyclopentanecarboxylic acid, cyclohexanecarboxylic acid, or any mixture thereof.

22. The method of claim 19, wherein the acidic solvent comprises sulfuric acid, hydrochloric acid, nitric acid, phosphonic acid, chloric acid, perchloric acid, hydrobromic acid, hydroiodic acid, or any mixture thereof.

23. The method of claim 14, wherein the hypervalent iodine oxyacid comprises $H_5IO_6$, $HIO_3$, $HIO_4$, $HIO_2$, HIO, or any mixture thereof, and/or the hypervalent iodine comprises 2-iodoxybenzoic acid (IBX), Dess-Martin periodinane (DMP), iodosylbenzene, iodosylarene of the formula Ar—I═O, bis(acetoxy)iodobenzene, bis(acetoxyoxy)iodoarenes of the formula Ar—I$(OCOCH_3)_2$, bis(trifluoroacetoxy)iodobenzene, bis(trifluoroacetoxyoxy)iodoarenes of the formula Ar—I$(OCOCF_3)_2$, wherein Ar is an unsubstituted aryl, or Ar is an aryl substituted with one or more of the following substituents: a $C_1$-$C_8$ alkyl, a $C_1$-$C_8$ alkoxy, a halide, and an electron-withdrawing group.

24. The method of claim 18, wherein the hypervalent iodine oxyacid comprises $H_5IO_6$, $HIO_3$, $HIO_4$, $HIO_2$, HIO, or any mixture thereof, and/or the hypervalent iodine comprises 2-iodoxybenzoic acid (IBX), Dess-Martin periodinane (DMP), iodosylbenzene, iodosylarene of the formula Ar—I═O, bis(acetoxy)iodobenzene, bis(acetoxyoxy)iodoarenes of the formula Ar—I$(OCOCH_3)_2$, bis(trifluoroacetoxy)iodobenzene, bis(trifluoroacetoxyoxy)iodoarenes of the formula Ar—I$(OCOCF_3)_2$, wherein Ar is an unsubstituted aryl, or Ar is an aryl substituted with one or more of the following substituents: a $C_1$-$C_8$ alkyl, a $C_1$-$C_8$alkoxy, a halide, and an electron-withdrawing group.

* * * * *